United States Patent
Jongerius et al.

(10) Patent No.: US 10,520,413 B2
(45) Date of Patent: Dec. 31, 2019

(54) PARTICLE SENSOR AND PARTICLE SENSING METHOD HAVING A SERIES OF SENSOR ELEMENTS

(71) Applicant: KONINKLIJKE PHILIPS N.V., Eindhoven (NL)

(72) Inventors: Michiel Johannes Jongerius, Eindhoven (NL); Koray Karakaya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 230 days.

(21) Appl. No.: 15/579,318

(22) PCT Filed: Jun. 3, 2016

(86) PCT No.: PCT/EP2016/062580
§ 371 (c)(1),
(2) Date: Dec. 4, 2017

(87) PCT Pub. No.: WO2016/198321
PCT Pub. Date: Dec. 15, 2016

(65) Prior Publication Data
US 2018/0164202 A1    Jun. 14, 2018

(30) Foreign Application Priority Data
Jun. 12, 2015  (EP) ................................. 15171840

(51) Int. Cl.
*G01N 15/02*   (2006.01)
(52) U.S. Cl.
CPC ............... *G01N 15/0255* (2013.01)

(58) Field of Classification Search
None
See application file for complete search history.

(56) References Cited

U.S. PATENT DOCUMENTS

| | | | |
|---|---|---|---|
| 5,616,872 A * | 4/1997 | O'Brien | G01N 15/0266 324/453 |
| 8,806,915 B2 * | 8/2014 | White | G01N 1/2273 73/24.02 |
| 2002/0014158 A1 | 2/2002 | Page | |

(Continued)

OTHER PUBLICATIONS

Chunghong He and Goodarz Ahmadi, "Particle deposition with Thermophoresis in Laminar an Duct Flows": Aerosol Science and Technology 29, 525-546, 1998.

(Continued)

*Primary Examiner* — Natalie Huls
*Assistant Examiner* — Jermaine L Jenkins

(57) ABSTRACT

Presented is a particle sensing system is for providing particle distribution information in a fluid flow in which thermophoretic particle movement is induced (10) towards a sensor (12) for sensing collected particles. In accordance with the present invention, the thermophoretic particle movement is in opposite direction to the direction of gravity, and the sensor (12) is located above the sensing volume. The sensor (12) comprises a series (70) of sensor elements arranged along the length direction of the elongate channel, each sensor element positioned for sensing a particular particle size. Additionally, a method providing particle distribution information in a fluid flow is presented.

13 Claims, 5 Drawing Sheets

(56) References Cited

U.S. PATENT DOCUMENTS

| | | | |
|---|---|---|---|
| 2004/0259267 A1 | 12/2004 | Gundel | |
| 2007/0039463 A1* | 2/2007 | Desmet | B01L 3/502753 95/45 |
| 2010/0288043 A1* | 11/2010 | Manalis | G01N 15/00 73/32 R |
| 2011/0197571 A1* | 8/2011 | Visser | G01N 27/4077 60/311 |
| 2013/0036793 A1 | 2/2013 | White | |
| 2013/0235357 A1* | 9/2013 | Delgado | G03F 7/70908 355/30 |

OTHER PUBLICATIONS

Igor Paprotny et al: 11 Microfabricated air-microfluidic sensor for personal monitoring of airborne particulate matter: Design, fabrication, and experimental results 11 , Sensors and Actuators A., vol . 201, Oct. 1, 2013 (Oct. 1, 2013), pp. 506-516.

J. Marra, On indoor air pollution with particles and its assessment with various particle sensors, PR-TN2009/00080.

K. Karakaya, "Gravimetric sensing of indoor aerosol concentration with a focus on PM2.5 mass concentration", PR-TN2013/00962.

James R. Brock, "On the theroy of thermal forces acting on aerosol particles", Journal of Colloid Science 17, pp. 768-780 (1962).

Z. Huang, Michae. Apte and Lara Gundel, "Termophoresis and it's Thermal Parameters for Aerosol Collection", Dec. 10, 2008, pp. 37-42, http://escholarship.org/uc/item/0mv367rb.

M.J. Jongerius, P.H. Bouma, D. Hayashi, G. Kooijman, O. Ouweltjes, R.F. Xue, and K. Karakaya, Evaluation of Shinyei PPD42 optical particle sensor, PR-TN2014/00237.

H. Grimm and D.J. Eatough, Aerosol Measurement: The Use of Optical Light Scattering for the Determination of Particulate Size Distribution, and Particle Mass, including the Semivolatile Fraction, Journal of the Aire&Waste Management Association 59, 101-107, 2009.

\* cited by examiner

PARTICLE SENSOR AND PARTICLE SENSING METHOD HAVING A SERIES OF SENSOR ELEMENTS

This application is the U.S. National Phase application under 35 U.S.C. § 371 of International Application No. PCT/EP2016/062580, filed on Jun. 3, 2016, which claims the benefit of International Application No. 15171840.0 filed on Jun. 12, 2015. These applications are hereby incorporated by reference herein.

FIELD OF THE INVENTION

This invention relates to sensors for detecting particles in a fluid flow.

BACKGROUND OF THE INVENTION

Airborne particle pollution, especially particle matter size less than 2.5 µm diameter range (named "PM2.5"), is a big concern for countries like China, where the speed of industrialization stretches the boundaries of regulatory requirements.

As a consequence of increasing consumer empowerment, the demand for information about the air quality of living spaces is increasing. Especially in China, excessive PM2.5 pollution has become a common problem in the last decade. This problem is also validated by continuous measurements in various Chinese cities. The data is publicly available and can be simultaneously monitored by mobile phone applications or through the web.

Availability of this data as well as continuous national and international media attention has created strong consumer awareness about the problem.

Official outdoor air quality standards define particle matter concentration as mass concentration per unit volume (e.g. $\mu g/m^3$). The average PM2.5 pollution concentration in mainland China has been calculated based on satellite data, and it has been found that the most of the country exceeds the World Health Organization limits of 10 $\mu g/m^3$, with some regions reaching and even exceeding PM2.5 concentrations of 100 $\mu g/m^3$.

Low cost particle sensors are for example based on the measurement of light scattered at the particles which are entrained by an air flow through a detection volume. The air flow is for example induced by a fan or a heater. Optical particle sensors typically give a particle count as the sensor output, and this information is then converted to a mass concentration. However, this conversion is usually not accurate, as different types of aerosols have different densities. Thus, the low cost optical approach does not easily enable discrimination between different particle sizes.

More expensive optical systems for professional use are available that also provide information on the size distribution of the particles in the air. However, these systems are more complex and expensive.

There are alternative sensor designs which collect particles and directly measure the total collected particle mass over time, for example using a gravimetric approach. Mass sensitive sensors do not however discriminate between the sizes of particles, and therefore do not provide information on the distribution of particle sizes in the air. Size specific particle detection (e.g. PM2.5) in conventional gravimetric systems therefore requires additional size classification approaches, such as cyclones, filters, impactors, etc., which increase the system complexity and generate a maintenance burden.

The mass measurement may for example be performed using a quartz crystal microbalance, a tapered resonator, an impactor, or weighing filters and sieves.

US2004259267A1 describes a system for particle exposure assessment for the measurement and identification of particulate content in gases. The application describes a particle size discriminator for discriminating between small and large particles. Thermographic force is used to capture all discriminated particles. After capturing, the particles are detected via mass or optical detection. US2002014158A1 describes a system for collecting particles in a fluid stream. Particles are collected by precipitating them on a surface via thermographic force. Precipitated particles are, optionally, analyzed.

US2013036793A1 describes an apparatus for measuring concentrations of air-born particulate matter. Bended channels are used to separate different sized particles. A collection surface is used to collect the separated particles.

US2011197571A1 presents a method for detecting particles in a gas flow and a particle sensor arrangement. By changing the temperature inside the arrangement particle build up on the sensor can be achieved. This particle buildup is detected by the sensor.

SUMMARY OF THE INVENTION

There is therefore a need for a particle sensor which can be implemented with low cost, but which provides particle size selectivity.

The invention is defined by the independent claims. The dependent claims define advantageous embodiments.

According to a first aspect of the invention, there is provided a particle sensing system for sensing particles entrained in a fluid flow, the particle sensing system comprising:

a sensing volume through which a fluid is to be passed having entrained particles, the sensing volume forms an elongate channel along which the fluid flows;

an arrangement for inducing thermophoretic particle movement in the fluid;

a sensor for sensing collected particles, wherein the arrangement is for inducing the thermophoretic particle movement upwardly, opposite to the direction of gravity, and the sensor is located at an upper end of the sensing volume;

the sensor (12) comprises a series (70) of sensor elements arranged along the length direction of the elongate channel, each sensor element positioned for sensing a particular particle size.

In this system, the force of gravity on the particles and the thermophoretic force are made to act in generally opposite directions. This enables a selectivity of particle size, since the gravitational force and the thermophoresis force have different functions with respect to particle size. In particular, the system implements a low pass filtering function with respect to particle size. The gravity force scales with the particle volume, i.e. the cube of the linear particle size, whereas the thermophoretic force scales in a different way. The fluid is for example a gas, such as air, or a liquid, such as water.

The sensing volume is located within the arrangement, for example between a heated and a cooling plate of the arrangement. As the fluid flows through the sensing volume, the sensing volume can be defined as fluid channel wherein the sensing volume has the shape of an elongate channel. The channel is elongate along the direction of the fluid flow.

The arrangement may comprise a heated plate at a lower end of the sensing volume. This provides a temperature gradient across the sensing volume in a vertical direction. The top of the sensing volume, where the sensor is located, is preferably maintained at a constant temperature. The heated plate may comprise a Peltier element or a resistive heating element. A temperature gradient may alternatively or additionally be obtained by means of a cooling element at a lower end of the sensing volume.

The arrangement may be adjustable to sequentially provide different thermal gradients in the sensing volume. Different thermal gradients will influence the filtering function, so that a particle size distribution may be obtained by applying different thermal gradients and analyzing the different measurement results.

The arrangement is for example operable to provide a thermal gradient in the sensing volume of at least 400 K/cm, more preferably at least 600 K/cm, and more preferably at least 800 K/cm. These thermal gradients are able to cause substantially all smaller particles to reach the sensor, for a desired length of the sensing volume such as in the range 10 mm to 100 mm, and a desired sensing volume height such as in the range 0.2 mm to 1 mm.

As mentioned above, the sensing volume comprises an elongate channel. The fluid flow is along the channel, to ensure the fluid flow remains in the channel for a sufficient time that the particles can move the required distance corresponding to the height the channel.
At different positions along the channel, different ranges of particle sizes will have had time to reach the sensor. Thus, the use of a set of sensor elements enables a particle size distribution to be determined.

According to an embodiment of the invention, different sensor elements are configured for sensing a different particle size. For example, one sensor element is configured for sensing particles having a first particle size and a second sensor element is configured for sensing particles having a second particle size, wherein the first particle size is different from the second particle size.

In one embodiment, one sensor element is a PM2.5 sensor and another sensor element is a PM10 sensor.

The sensor may comprise a mass sensor. This may for example be a mass sensor crystal. The mass detection is then based on the effect on the resonant frequency of the particles in contact with the sensor, which have become stuck (e.g. electrostatically or physically) to the sensor surface.

Alternatively, the sensor may comprise an optical sensor. This may use light scattering or light reflection to assess the particle mass, for example through a transparent upper wall of the sensing volume.

A flow controller may be provided for controlling a flow speed of fluid through the sensing volume. By controlling the flow rate, particle size distribution may be obtained. In particular, at different flow rates, different ranges of particle size will have time to reach the sensor within the length of the sensing volume.

A means may be provided for controlling a vertical height of the sensing volume. By controlling the height of the sensing volume, which represents the (maximum) distance over which particles need to move to reach the sensor, particle size distribution may be obtained. In particular, different vertical heights will mean that different ranges of particle size will have time to reach the sensor within the length of the sensing volume. The means may be a mechanical means to change the volume of the sensing volume. For example, the volume may be changed by changing the distance between a heating plate (10) and a mass sensing plate (12) as illustrated in FIG. 1.

Examples in accordance with another aspect of the invention provide a particle sensing method for sensing particles entrained in a fluid flow, the method comprising:
  passing a fluid having entrained particles through a sensing volume;
  inducing thermophoretic particle movement in the fluid;
  sensing collected particles,
  wherein the heating induces thermophoretic particle movement upwardly, opposite to the direction of gravity, and the sensing is in respect of particles located at an upper end of the sensing volume; and
  wherein sensing collected particles is performed by independently sensing the collected particles at a plurality of positions along a length direction of the sensing volume.

This method combines the force of gravity on the particles and the thermophoresis force to enable a selectivity of particle size, implementing a low pass filtering function with respect to particle size.

The method may comprise sequentially adjusting heating to provide different thermal gradients in the sensing volume. A particle size distribution may then be obtained by sequentially applying different thermal gradients.

As the method comprises independently sensing the collected particles at a plurality of positions along a length direction of the sensing volume, a particle size distribution may then be determined based on the multiple sensor measurements.

A flow speed of fluid through the sensing volume may be controlled. A particle size distribution may again be obtained by combining the sensor information for different flow rates.

A vertical height of the sensing volume may be controlled. In this case, a particle size distribution may be obtained by controlling the height of the sensing volume.

According to an embodiment of the invention, at each of the plurality of positions of the sensor elements along the length direction of the sensing volume, a different particle size is sensed.

These different approaches for enabling a particle size distribution may be used in any combination, for example with any two or three different control parameters selected from the options listed above. By varying these parameters, different sensing information is obtained. All of the gathered sensing information can then be combined to derive the desired particle size distribution.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a particle sensing system for sensing particles entrained in a fluid flow in which heating is used to induce thermophoretic particle movement towards a sensor for sensing collected particles. The thermophoretic particle movement is in opposite direction to the direction of gravity, and the sensor is located upwardly above the sensing volume. This enables a selectivity of particle size, since the gravitational force and the thermophoresis force have different functions with respect to particle size. Note that the thermophoresis force is generally vertically upwardly, but it may be inclined by an acute angle to the perfect vertical. The term "upwardly" and "opposite to the direction of gravity" should be understood accordingly. In particular, the electrophoretic force will at least have a component which is indeed perfectly vertically upward.

The use of thermophoresis is known for inducing particles in air to deposit on the surface of a mass sensor. For example reference is made to I. Paprotny, F. Doering, P. A. Solomon, R. M. White, and L. A. Gundel, "Microfabricated air-microfluidic sensor for personal monitoring of airborne particulate matter": Design, fabrication, and experimental results, Sensors and Actuators A201, 506-516, 2013.

Figure 1:
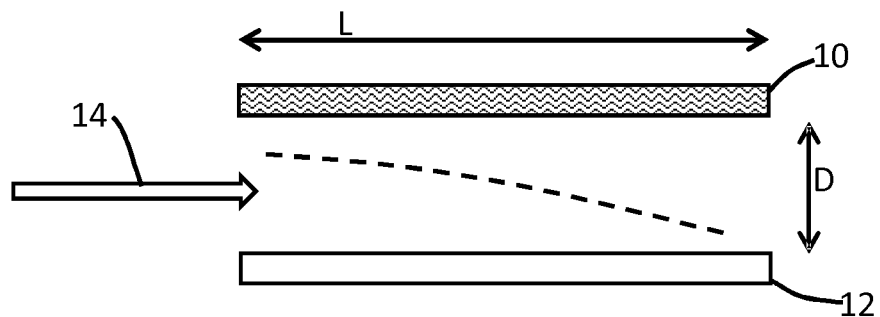
FIG. 1 shows a known particle measurement system based on the thermophoresis effect.

FIG. 1 shows the principle of this process. The sensor comprises a heating plate 10 disposed above a mass sensing plate 12. An air stream 14 with entrained particles is directed to flow between the two surfaces with a velocity $v_g$. The space between the two surfaces is defined as the sensing volume which is an elongate channel. The top surface is kept at a higher temperature than the bottom surface.

Due to the gradient in temperature, the particles experience a thermophoresis force, and a resulting vertical velocity $v_{th}$, driving the particles towards the surface with the lowest temperature. As a result, the particles that are below the dashed line in FIG. 1 will arrive at the bottom plate (assuming a plug flow, for simplicity).

The fraction of the entering particles arriving at the bottom plate is given by $L/D*v_{th}/v_g$, with a maximum value of 1. L and D are the length and spacing distance, respectively.

All particles are collected if $L>L_c$ where $L_c=(Vg/Vth)*D$.

This is the case in the system proposed in the Paprotny reference above, where in the bottom surface a mass sensor is integrated for measuring the total collected mass of particles.

Figure 2:
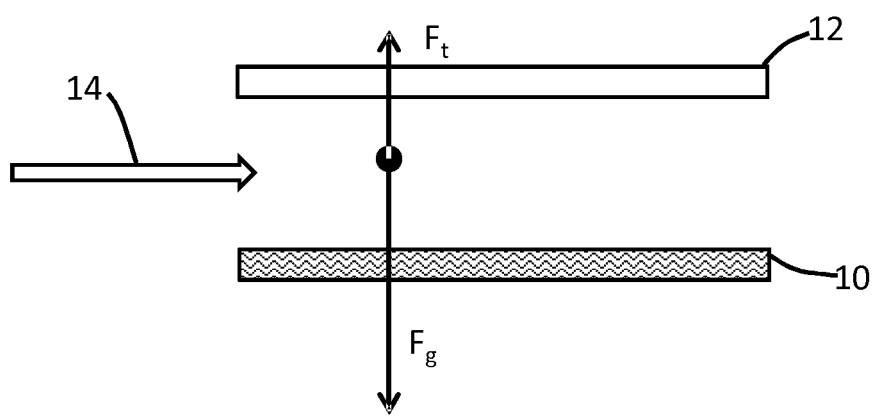
FIG. 2 shows a first example of a particle measurement system based on the thermophoresis effect in accordance with the invention.
Figure 3:
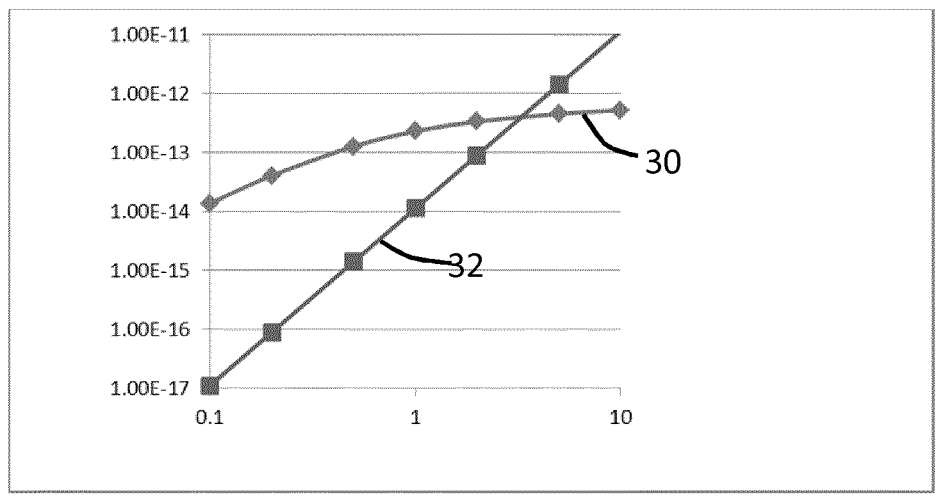
FIG. 3 shows the resulting thermophoresis and gravity forces as a function of particle size for the system of FIG. 2.
Figure 4:
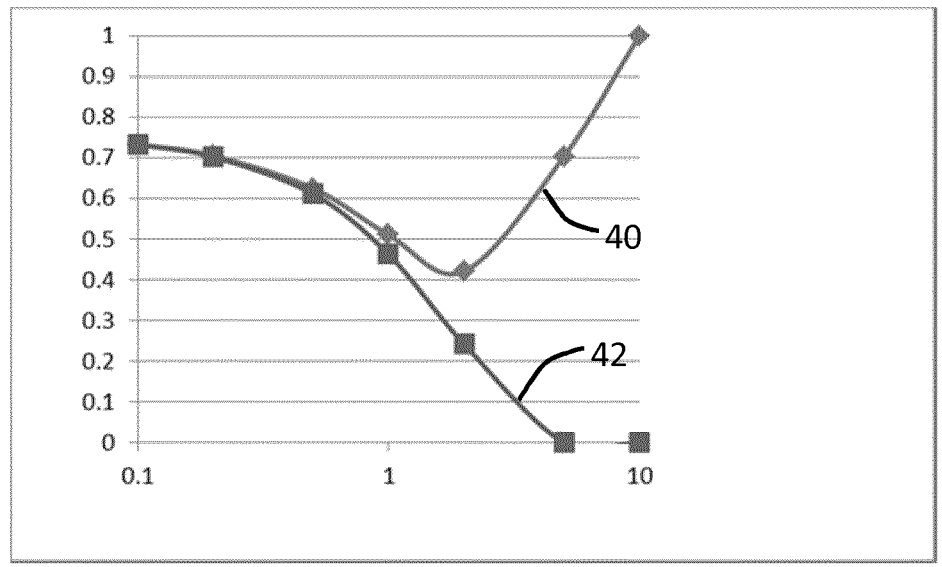
FIG. 4 shows the collection efficiency for the detection of particles using the system of FIG. 2.

FIG. 2 shows in schematic form an example of an implementation in accordance with the concepts underlying the invention. The sensor comprises the heating plate 10 disposed below the mass sensing plate 12. An air or other fluid stream 14 with entrained particles is again directed to flow between the two surfaces. The heating arrangement is in this way for inducing thermophoretic particle movement upwardly, or with an upward component, generally opposite to the direction of gravity. The heating arrangement may include heating on one side and cooling on the other. The temperature on both sides may be controlled to maintain a constant temperature difference, with controlled heating on both sides, or heating and cooling. However, heating on one side only to provide a relative increase in temperature compared to the ambient temperature may also be sufficient.

A particle experiences a downward gravitational force $F_g$ and an upward thermophoresis force $F_t$. The thermophoresis force will thus pull the particles upwards, while at the same time the gravity force pulls the particles downwards. The net force will determine whether the particles will move upwards or downwards. This feature is exploited for providing a size specific particle sensing mechanism, by eliminating the large particles on the detector surface. In this way, a specific combination of thermophoresis force and gravity force is used to create a sensor to selectively collect particles below a given particle size.

A model for analyzing the thermophoresis effect is disclosed in Chunhong He and Goodarz Ahmadi, "Particle deposition with Thermophoresis in Laminar and Turbulent Duct Flows": Aerosol Science and Technology 29, 525-546, 1998. This approach has been used in the examples below to model the particle behavior.

A first model is based on analyzing the thermophoresis force on NaCl particles in air (with a particle density of 2165 $kg/m^3$) through a 71 mm long (L=71 mm), 30 mm wide, and 0.38 mm high (D=0.38 mm) channel, at a gas flow speed of 585 mm/s (equivalent to 400 ml/min).

The heated plate is modeled to be at 52.7° C., and the sensor side held at a constant temperature of 20.9° C., corresponding to a temperature gradient of 837 K/cm.

FIG. 3 shows the resulting thermophoresis and gravity forces as a function of particle size. Plot 30 is the thermophoresis force, and plot 32 is the gravitational force. The x-axis is the particle diameter in μm and the y-axis is the force in N. The axes have a logarithmic scale. Thus, the cubic relationship between the gravity force and the particle linear size (since the gravitational force is proportional to the mass and therefore volume, which is proportional to the linear particle size cubed) is seen as a straight line with gradient of 3.

The gravity force is found to be larger than the thermophoresis force for particles larger than 4 μm diameter. These particles will move towards the heated bottom plate and will therefore not reach the top sensor plate to be detected. The detector will thus only detect particles smaller than 4 μm diameter for this example.

FIG. 4 shows the collection efficiency for the detection of the NaCl particles. Plot 40 shows the effect of gravity and thermophoresis force working in the same direction (as in FIG. 1), and plot 42 shows the effect of gravity and thermophoresis force working in the opposite directions (as in FIG. 2). The x-axis is the particle diameter in μm and the y-axis is collection efficiency, i.e. the proportion of the particles that are collected. The x-axis has a logarithmic scale.

FIG. 4 shows that for 100 nm particles, the role of the thermophoresis force is dominant and the particle collection efficiency is about 70% (for both examples).

For the system of FIG. 1, for increasing particle size, the collection efficiency first decreases due to the fact that the thermophoresis force does not increase fast enough to compensate for the increased drag force by the viscosity of the air. Then, for larger particles the gravity force sets in leading in the conventional approach to an increase of the collection efficiency due to this gravity force working in the same direction as the thermophoresis force.

For the system of FIG. 2, the gravity force on the large particles will prevent them from reaching the sensor surface (the top surface in this case) and particles larger than 4 μm will not reach the mass sensor.

A second model is based on analyzing the thermophoresis force on dry clay particles in air (with a particle density of 1600 kg/m$^3$) for different temperature gradients (382 K/cm, 782 K/cm and 1580 K/cm). The model is based on a channel which is 10 mm long, 10 mm wide and 0.5 mm high, and with a gas flow of 10 ml/min. These dimensions are in line with the typical size of a sensor crystal of about 10×10 mm for detecting particle mass. It is assumed that the sensor side is kept at a temperature of 21° C., while the heated plate, acting as the thermophoresis force driver, is set at 40° C., 60° C., and 100° C., respectively, giving rise to the different temperature gradients.

Figure 5:
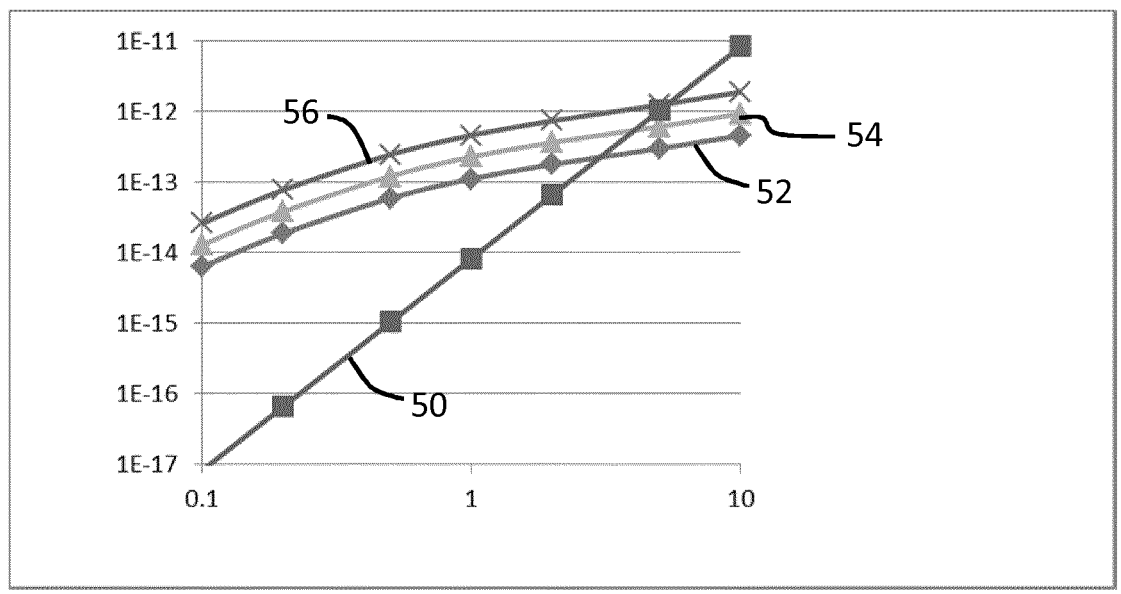
FIG. 5 shows the gravity force and the thermophoresis forces for various values of an applied temperature gradient.

FIG. 5 shows the gravity force as plot 50 and the thermophoresis forces (plots 52, 54 56) for various values of the applied temperature gradient. Plot 52 is for 382 K/cm, plot 54 is for 782 K/cm and plot 56 is for 1580 K/cm. The x-axis is the particle diameter in μm and the y-axis is the force in N. The axes have a logarithmic scale.

For particle diameters larger than about 3.0 μm, 4.0 μm, and 5.4 μm, respectively, the gravity force on the particle is larger than the thermophoresis force and the particle is driven towards the lower plate. Hence, the temperature gradient setting can be used to set the particle size boundary value above which the gravity force leads to a net vertical particle velocity in the direction of the gravity force.

Figure 6:
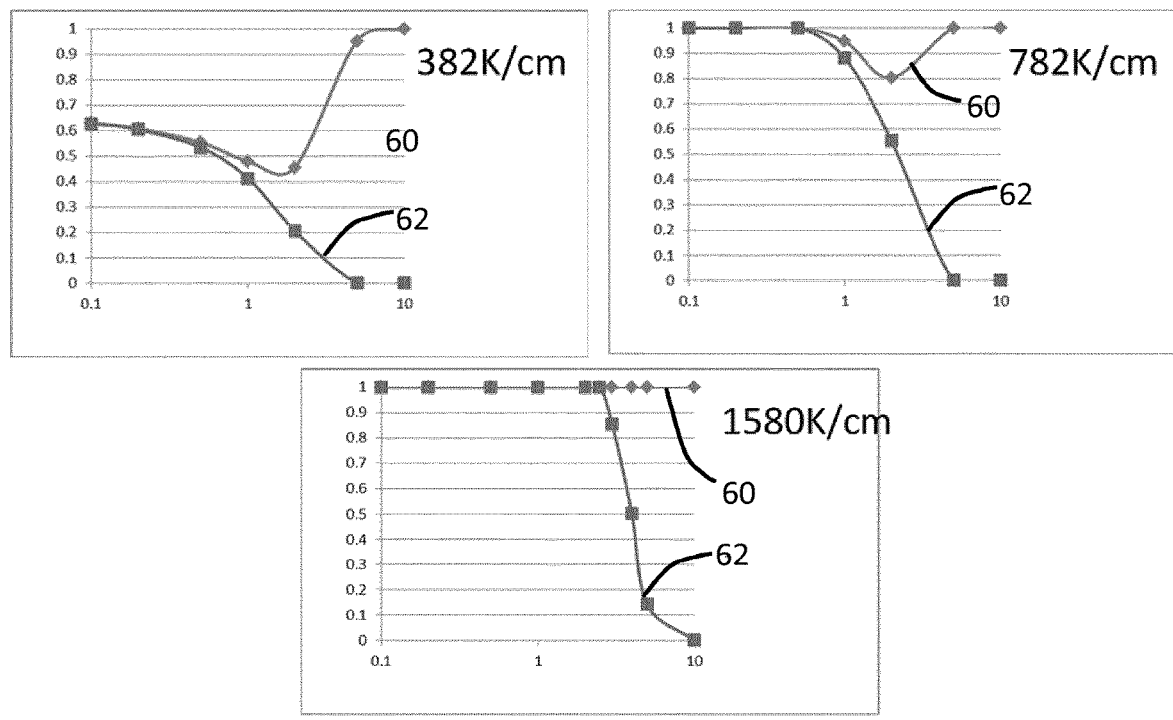
FIG. 6 shows the particle collection efficiency for each thermal gradient used in FIG. 5.

FIG. 6 shows the particle collection efficiency for each thermal gradient, and also a comparison with the system of FIG. 1. Plot 60 in each case shows the effect of gravity and thermophoresis force working in the same direction (as in FIG. 1), and plot 62 in each case shows the effect of gravity and thermophoresis force working in the opposite directions (as in FIG. 2). The x-axis is again the logarithmic particle diameter in μm and the y-axis is collection efficiency.

A temperature gradient of 382 K/cm is insufficient to drive all small particles in the channel towards the sensor surface. However, all particles that are smaller than about 1 μm are collected at 782 K/cm. The upper limit of collected particles size shifts to about 2.5 μm if the gradient is further increased to 1580 K/cm. This condition is in a close agreement with the requirements for a PM2.5 particle detector. At 75 μg/m$^3$ particle concentration in the air, the total collected mass is 0.75 ng/min.

The basic sensor example given above is able to detect a range of particle sizes below a threshold, and this threshold may be adjusted by varying the thermal gradient. By operating the sensor at different temperatures, particle size distribution information may be obtained. For example the difference between the sensed mass for the 782 K/cm and 1580 K/cm readings relates to particles in the range 1 μm to 2.5 μm. Thus a particle size distribution may be obtained using the sensor design shown.

Figure 7:
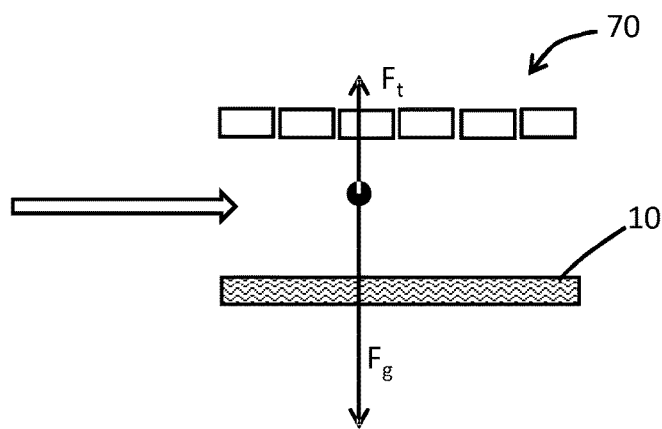
FIG. 7 shows a second example of a particle measurement system based on the thermophoresis effect in accordance with the invention.

FIG. 7 shows a second example of sensor design for providing particle distribution information.

Information on the size distribution of particles in the air is obtained by replacing the single sensor 12 in the collecting surface of the channel in FIG. 2 with an array 70 of mass sensors, each covering a part of the top surface of the channel.

As an example, the collection efficiency of dry clay particles in a channel of 10 mm wide, 60 mm long and 0.5 mm high is calculated, using six sensor positions of 10×10 mm size each. The air flow is assumed to be 60 ml/s.

Figure 8:
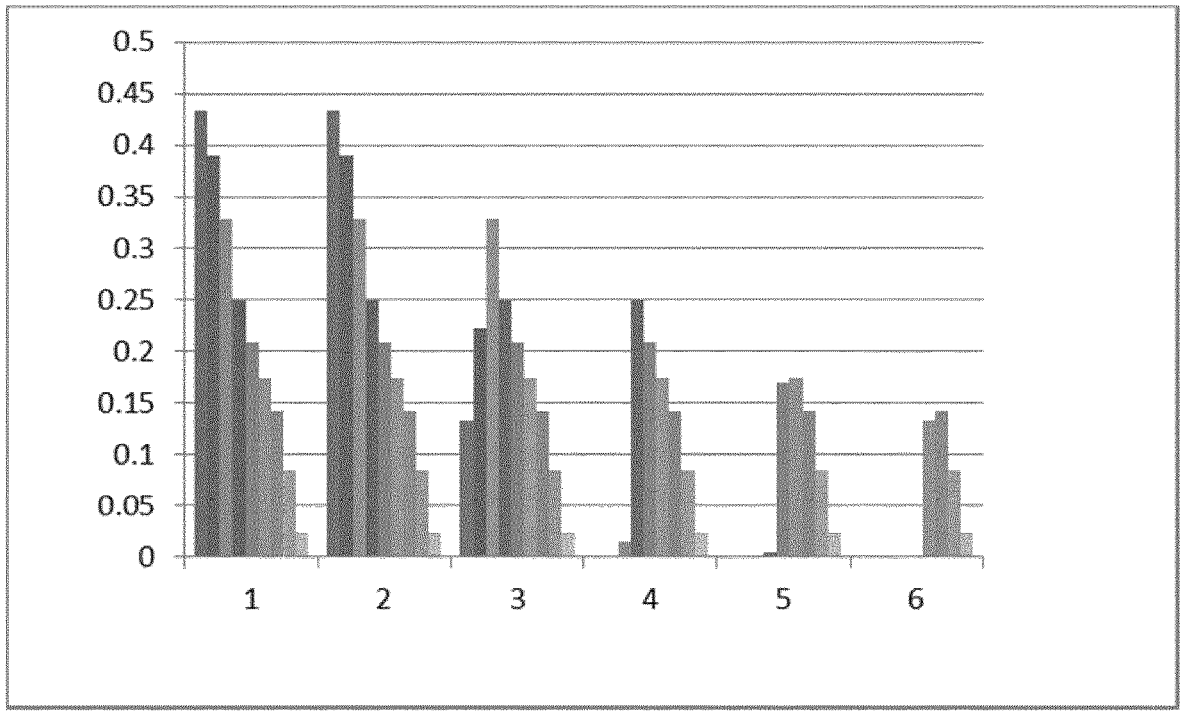
FIG. 8 shows the collection efficiency for the detection of particles using the system of FIG. 7.

The result is shown in FIG. 8.

The x-axis shows the sensor position and the y-axis is the collection efficiency. Each sensor position is modeled for 8 different particle sizes: 0.1 μm, 0.4 μm, 0.8 μm, 1.5 μm, 2.0 μm, 2.5 μm, 3.0 μm, 4.0 μm and 5.0 μm. The particle sizes are plotted from left to right. Thus for sensor position 1, the collection efficiency for particle sizes of 0.1 μm is 0.43 (the leftmost tallest bar) whereas the collection efficiency for particle sizes of 5.0 μm is 0.02 (the rightmost shortest bar).

Particles larger than 5 μm are hardly collected on the sensors in the channel at all. On sensor 6, only particles between 2.5 μm and 4 μm size are collected. Up to sensor 5, also particles of 2.0 μm are collected. Particles of 1.5 μm are collected up to sensor 4, and particles of 0.8 μm up till sensor 3. Sensors 1 and 2 also collect smaller particles. They provide almost identical results.

It might therefore be that sensor position 1 should be left blank since that sensor position might also suffer from a non-uniform flow profile at the channel entry.

This example illustrates clearly the capabilities of the system not only in excluding large particles, but also providing information on the size distribution of particles in the air.

In the two embodiments above, integrated mass sensors may be used in the receiving surface of the channel. These mass sensors measure a resonant frequency of a resonant structure, and this resonant frequency is influenced by the mass of particles in contact with the sensor surface.

It is also possible to measure the presence of collected particles on a surface by optical means, such as by light scattering or light reflection. The collecting surface then needs to be optically transparent to provide light access to the positions of collected particles.

It is clear from the examples above that the temperature gradient may be varied, or a segmented electrode design may be used, to provide distribution information. In the case of temperature gradient control, different temperature settings of the heater are used. By sweeping over a temperature range, or a stepwise operation of the temperature setting, it is possible to tune the size range of particle deposited on the detector surface.

In another example, the sensor system is operated in such a way that the fluid flow speed (air velocity) is utilized for size screening of particles, but operating in a constant thermal gradient mode. It is clear from the explanations above that the deposited particle size range is dependent on the air velocity; i.e. a slower air velocity will result in collection of particles up to a larger size range, and vice versa.

Figure 9:
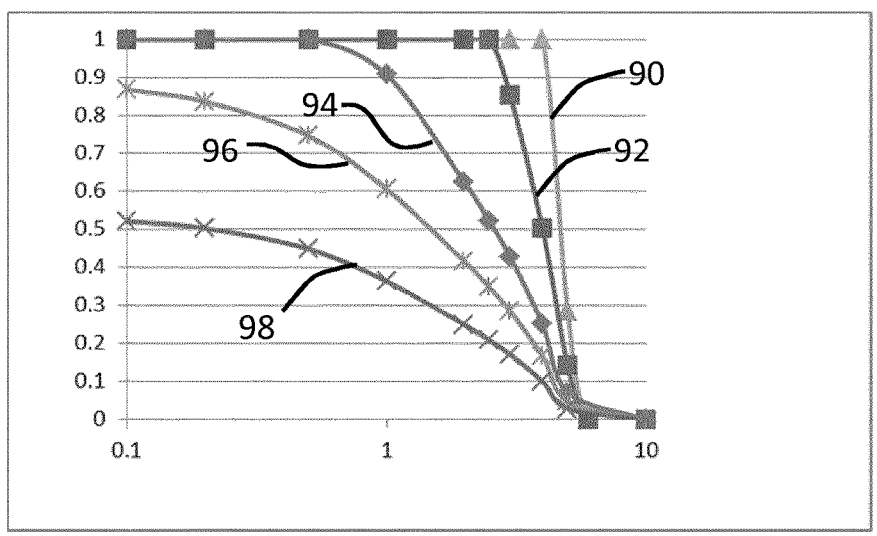
FIG. 9 shows the use of a sensor as in FIG. 2 at different flow rates.

FIG. 9 shows the results of the use of a sensor as in FIG. 2 for the detection of clay particles as in the model above, at a temperature gradient of 1580 K/cm. As in the example above, the particle density is 1600 kg/m$^3$ and with sensing using a channel which is 10 mm long, 10 mm wide and 0.5 mm high.

Plot 90 is for a flow of 5 ml/min, plot 92 is for a flow of 10 ml/min, plot 94 is for a flow of 20 ml/min, plot 96 is for a flow of 30 ml/min and plot 98 is for a flow of 50 ml/min.

It can be seen that the collection efficiency of small particles decreases below 1 if the air flow is above 20 ml/min. This efficiency can however be increased by increasing the length of the channel.

The distance between the heater plate and the sensor (e.g. a resonating gravimetric detector) may also be used as a parameter for manipulating the size detection range of the sensor. This distance is shown as D in FIG. 1.

By employing a mechanical design, for example with a setting screw or mechanical driver, and by changing the distance between the heater and the detector, the size range of the detector can be tuned. A shorter distance will lead to a deposition of a larger particle size range, whereas a larger distance will result a sensor system for a smaller particle size range.

Figure 10:
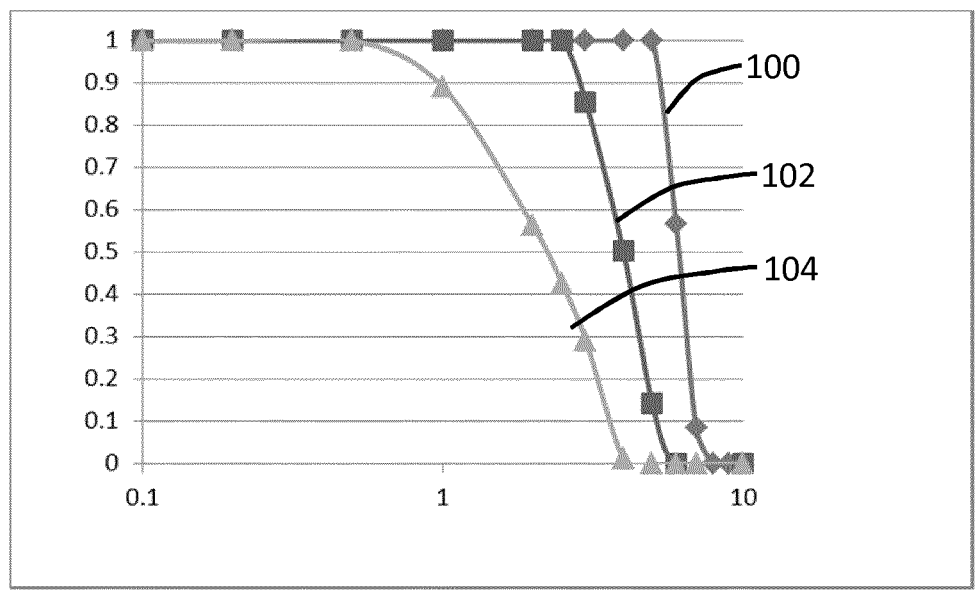
FIG. 10 shows the use of a sensor as in FIG. 2 with different channel heights.

FIG. 10 shows the use of a sensor as in FIG. 2 for the detection of clay particles as in the model above, at a temperature gradient of 1580 K/cm. As in the example above, the particle density is 1600 kg/m$^3$ and with sensing using a channel which is 10 mm long, 10 mm wide and with variable height. The air flow is 10 ml/min.

Plot 100 is for D=0.25 mm, plot 102 is for D=0.5 mm and plot 104 is for D=1.0 mm.

Some of these examples allow multiple size range operation, which can be utilized for selecting the sensor operation range; e.g. PM1, PM2.5 and PM10, with the same sensor unit.

This invention is of interest for particle sensors (e.g. PM2.5) for indoor climate control, but also for outdoor sensor devices, adding the feature that besides a total mass also information on the particle size distribution can be derived. It offers the potential for monitoring changes in aerosol concentrations and types, e.g. by all kinds of indoor activities, such as cooking or smoking, and can also provide the essential control feedback to air purifier devices.

As well as being applicable to measurement of particles in air (or other gases), similar approaches can be adopted for particle sensors in fluids, for example in water quality monitoring and control systems.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A particle sensing system for providing particle size distribution information, the particle sensing system comprising:
    a sensing volume through which a fluid is to be passed having entrained particles;
    an arrangement for inducing a thermophoretic particle movement in the sensing volume;
    a sensor for sensing collected particles,
    wherein the arrangement is for inducing the thermophoretic particle movement upwardly, opposite to the direction of gravity, and the sensor is located at an upper end of the sensing volume, and
    wherein the sensing volume forms an elongate channel and wherein the fluid flows along the channel, wherein
    the sensor comprises a series of sensor elements arranged along the length direction of the elongate channel, each sensor element positioned for sensing a particular particle size.

2. A particle sensing system as claimed in claim 1, wherein the arrangement comprises a heated plate at a lower end of the sensing volume.

3. A particle sensing system as claimed in claim 1, wherein the arrangement is adjustable to sequentially provide different thermal gradients in the sensing volume.

4. A particle sensing system as claimed in claim 1, wherein the arrangement is operable to provide a thermal gradient in the sensing volume of at least 400 K/cm, more preferably at least 600 K/cm, and more preferably at least 800 K/cm.

5. A particle sensing system as claimed in claim 1, wherein the sensor comprises a mass sensor.

6. A particle sensing system as claimed in claim 1, wherein the sensor comprises an optical sensor.

7. A particle sensing system as claimed in claim 1, comprising a flow controller for controlling a flow speed of fluid through the sensing volume.

8. A particle sensing system as claimed in claim 1, wherein different sensor elements of the series of sensor elements are configured for sensing a different particle size.

9. A particle sensing system as claimed in claim 8, wherein one sensor element of the series of sensor elements is a PM2.5 particle sensor and wherein another sensor element of the series of sensor elements is a PM10 particle sensor.

10. A particle sensing method for providing particle size distribution information, the method comprising:
    passing a fluid having entrained particles through a sensing volume;
    inducing thermophoretic particle movement in the sensing volume;
    sensing collected particles, and
    wherein the thermophoretic particle movement is induced upwardly, opposite to the direction of gravity, and the sensing is in respect of particles located at an upper end of the sensing volume
    wherein:
    sensing collected particles is performed by independently sensing the collected particles at a plurality of positions along a length direction of the sensing volume.

11. A particle sensing method as claimed in claim 10, comprising sequentially adjusting heating to provide a different thermal gradient in the sensing volume.

12. A particle sensing method as claimed in claim 10, comprising controlling a flow speed of fluid through the sensing volume.

13. A particle sensing method as claimed in claim 10, wherein at each of the plurality of positions a different particle size is sensed.

* * * * *